US00PP15215P2

(12) United States Plant Patent
Yomo et al.

(10) Patent No.: US PP15,215 P2
(45) Date of Patent: Oct. 12, 2004

(54) ***SALVIA* PLANT NAMED 'SUNSARUPIN'**

(50) Latin Name: *Salvia jamensis*
Varietal Denomination: Sunsarupin

(75) Inventors: Yasunori Yomo, Kawasaki (JP); Takuro Ishihara, Youkaichi (JP)

(73) Assignee: Suntory Flowers, Lmtd., Tokyo (JP)

( * ) Notice: Subject to any disclaimer, the term of this patent is extended or adjusted under 35 U.S.C. 154(b) by 19 days.

(21) Appl. No.: 10/716,049

(22) Filed: Nov. 18, 2003

(51) Int. Cl.[7] ..... A01H 5/00
(52) U.S. Cl. ..... Plt./226
(58) Field of Search ..... Plt./226

*Primary Examiner*—Kent Bell
(74) *Attorney, Agent, or Firm*—C. A. Whealy

(57) ABSTRACT

A new and distinct cultivar of *Salvia* plant named 'Sunsarupin', characterized by its upright and relatively compact plant habit; freely basal branching habit; dense and bushy plant form; freely flowering habit; dark pink-colored flowers; and tolerance to high and low temperatures.

1 Drawing Sheet

Botanical classification/cultivar designation: *Salvia jamensis* cultivar Sunsarupin.

BACKGROUND OF THE INVENTION

The present Invention relates to a new and distinct cultivar of *Salvia* plant, botanically known as *Salvia jamensis,* and hereinafter referred to by the name 'Sunsarupin'.

The new *Salvia* is a product of a planned breeding program conducted by the Inventors in Yokaichi-shi, Shiga, Japan. The objective of the breeding program was to create new compact *Salvia* cultivars with bushy growth habit and numerous flowers with attractive coloration.

The new *Salvia* originated from a cross-pollination made by the Inventors in April, 1998 of a proprietary *Salvia* selection identified as code number 97S34-2, not patented, as the female, or seed, parent with the *Salvia jamensis* cultivar La Luna, not patented, as the male, or pollen, parent. The new *Salvia* was discovered and selected by the Inventors as a single flowering plant within the progeny of the stated cross-pollination grown in a controlled environment in Yokaichi-shi, Shiga, Japan.

Asexual reproduction of the new cultivar by cuttings and divisions taken at Yokaichi-shi, Shiga, Japan, since September, 2000, has shown that the unique features of this new *Salvia* are stable and reproduced true to type in successive generations.

SUMMARY OF THE INVENTION

Plants of the cultivar Sunsarupin have not been observed under all possible environmental conditions. The phenotype may vary somewhat with variations in environment such as temperature and light intensity without, however, any variance in genotype.

The following traits have been repeatedly observed and are determined to be the unique characteristics of 'Sunsarupin'. These characteristics in combination distinguish 'Sunsarupin' as a new and distinct *Salvia* cultivar:

1. Upright and relatively compact plant habit.
2. Freely basal branching, dense and bushy plant form.
3. Freely flowering habit.
4. Dark pink-colored flowers.
5. Tolerant to high and low temperatures.

Plants of the new *Salvia* differ from plants of the parents primarily in flower color as plants of the female parent selection have red purple-colored flowers and plants of the male parent, the cultivar La Luna, have yellow green-colored flowers.

Plants of the new *Salvia* differ from plants of the *Salvia* cultivars Sunsaruki, U.S. Plant patent application Ser. No. 10/716,055, and Sunsaruoro, U.S. Plant patent application Ser. No. 10/716,056 primarily in flower color.

Plants of the new *Salvia* can be compared to plants of the *Salvia* cultivar Orchestra Red, not patented. In side-by-side comparisons conducted in Yokaichi-shi, Shiga, Japan, plants of the new *Salvia* differed from plants of the cultivar Orchestra Red in the following characteristics:

1. Plants of the new *Salvia* were more compact than plants of the cultivar Orchestra Red.
2. Plants of the new *Salvia* had shorter internodes and were bushier than plants of the cultivar Orchestra Red.
3. Plants of the new *Salvia* had shorter leaves than plants of the cultivar Orchestra Red.
4. Plants of the new *Salvia* had larger flowers than plants of the cultivar Orchestra Red.
5. Plants of the new *Salvia* had more flowers per lateral stem than plants of the cultivar Orchestra Red.
6. Plants of the new *Salvia* and the cultivar Orchestra Red differed in flower color as plants of the cultivar Orchestra Red has red-colored flowers.
7. Plants of the new *Salvia* were tolerant to lower temperatures than plants of the cultivar Orchestra Red.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Salvia.*

The photograph at the top of the sheet comprises a side perspective view of a typical flowering plant of 'Sunsarupin' grown in a container.

The photograph at the bottom of the sheet comprises a close-up view of typical flowers of 'Sunsarupin'.

DETAILED BOTANICAL DESCRIPTION

Plants shown in the aforementioned photographs and used in the following description were grown under conditions which closely approximate commercial production conditions from April to October, 2002 in a polyethylene-covered greenhouse in Yokaichi-shi, Shiga, Japan. During the production of the plants, day temperatures were about 25° C. and night temperatures were about 20° C. Plants in the photographs and used for the description were about six months old when the photographs and description were taken.

In the following description, color references are made to The Royal Horticultural Society Colour Chart, 2001 Edition, except where general terms of ordinary dictionary significance are used.

Botanical classification: *Salvia jamensis* cultivar Sunsarupin.

Parentage:

*Female, or seed, parent.*—Proprietary selection of *Salvia jamensis* identified as code number 97S34-2, not patented.

*Male, or pollen, parent.*—*Salvia jamensis* cultivar La Luna, not patented.

Propagation:

*Type.*—By cuttings.

*Time to initiate roots.*—Summer: About 7 days at 25° C. Winter: About 10 days at 20° C.

*Time to produce a rooted young plant.*—Summer: About 30 days at 20 to 30° C. Winter: About 40 days at 15 to 20° C.

*Root description.*—Fine, fibrous, freely branching and light brown in color.

Plant description:

*Form.*—Perennial. Mostly upright and relatively compact plant habit; narrow inverted triangle. Freely basal branching with about 20 flowering stems per plant; dense and bushy plant habit; vigorous growth habit. Flowers arranged in verticillasters on spikes.

*Plant height.*—About 59 cm.

*Plant width.*—About 50 cm.

*Flowering stem description* (*peduncles*).—Length: About 45 cm. Diameter: About 3 mm. Internode length: About 4.5 cm. Strength: Strong. Texture: Smooth, glabrous. Color: 144A.

*Foliage description.*—Arrangement: Opposite, simple. Length: About 2.2 cm. Width: About 1.6 mm. Shape: Ovate. Apex: Acute. Base: Obtuse. Margin: Serrate to crenate. Texture, upper and lower surfaces: Rough; waxy; glabrous. Venation pattern: Pinnate. Color: Developing and fully expanded foliage, upper surface: 146A. Developing and fully expanded foliage, lower surface: 146C. Petiole: Length: About 1.3 cm. Diameter: About 0.7 mm. Texture, upper and lower surfaces: Smooth, glabrous. Color: 145A.

Flower description:

*Flower arrangement and shape.*—Single bilabiate flowers in verticillasters on spikes; flowers face upright and outwardly. Freely flowering, about 12 flowers and flower buds per spike.

*Natural flowering season.*—Continuous from spring to late autumn in Japan.

*Flower longevity on the plant.*—Individual flowers last about two to five days on the plant. Flowers not persistant.

*Fragrance.*—Faintly fragrant; sweet.

*Flower buds.*—Length: About 1.5 mm. Diameter: About 3 mm. Shape: Oblong. Color: 50B.

*Inflorescence size.*—Length: About 24 cm. Diameter: About 6 cm.

*Flowers.*—Diameter: About 2 cm. Depth (height): About 3 cm.

*Petals.*—Arrangement: Bilabiate; one upper lip and one lower lip with two lobes; lips fused at the base. Length: Upper petal: About 9 mm. Lower petal: About 1.2 cm. Width: Upper petal: About 3 mm. Lower petal: About 1.5 cm. Shape: Upper petal: Broadly elliptic; hooded. Lower petal: Roughly orbicular. Apex: Upper petal: Hooked. Lower petal: Two-lobed. Margin, upper and lower petals: Entire. Texture, upper and lower petals: Satiny, smooth. Color, upper and lower petals: When opening and fully opened, upper surface: 69D underlain with 52C. When opening and fully opened, lower surface: 69D underlain with 48C.

*Sepals.*—Arrangement: Two sepals fused into a tube. Length: About 3 mm. Width: About 2.7 mm. Shape: Triangular. Apex: Acute. Margin: Entire. Color, upper and lower surfaces: 144B overlain with 187A.

*Pedicels.*—Strength: Moderately strong. Length: About 1.5 mm. Diameter: About 0.3 mm. Aspect: About 40° from vertical. Texture: Smooth, glabrous. Color: 147A.

*Reproductive organs.*—Stamens: Quantity per flower: Two. Anther shape: Ovate. Anther length: About 8 mm. Anther color: 15C. Pollen amount: Moderate. Pollen color: 15A. Pistils: Quantity per flower: One. Pistil length: About 2.7 cm. Stigma shape: Two-parted. Stigma color: 48D. Style length: About 2.5 cm. Style color: 155C. Ovary color: 3C.

*Seed/fruit.*—Seed and fruit production has not been observed.

Disease/pest resistance: Plants of the new *Salvia* have not been noted to be resistant to pathogens and pests common to *Salvia*.

Temperature tolerance: Plants of the new *Salvia* have been observed to tolerate temperatures from −10 to 40° C.

It is claimed:

1. A new and distinct cultivar of *Salvia* plant named 'Sunsarupin', as illustrated and described.

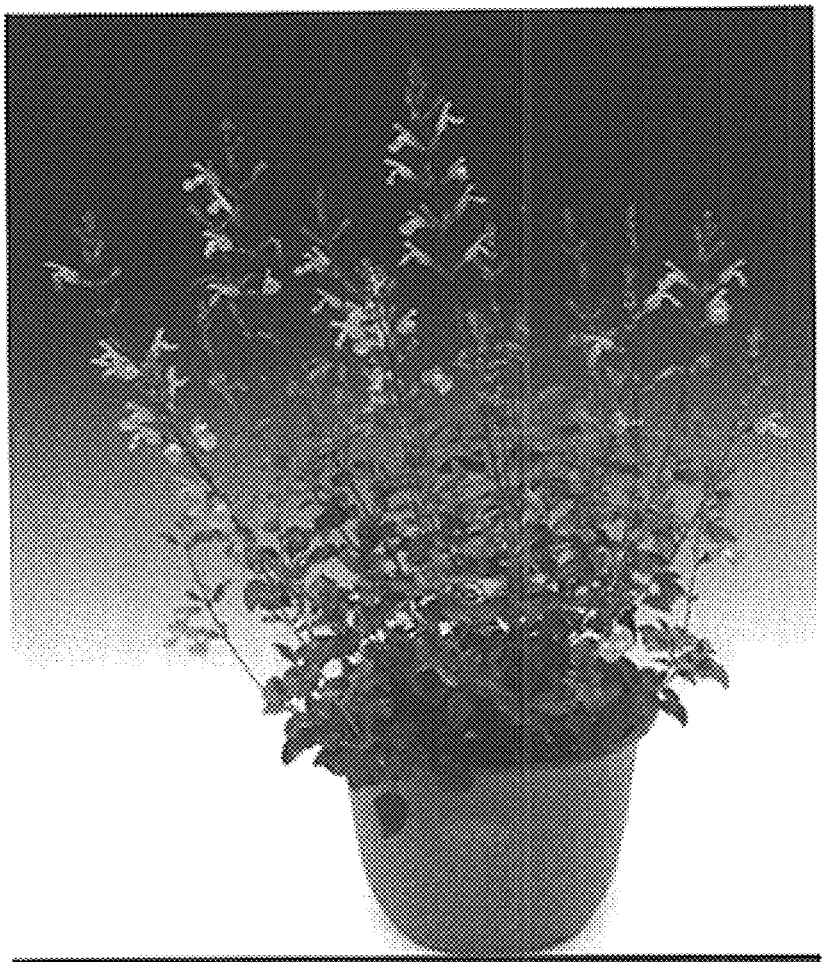
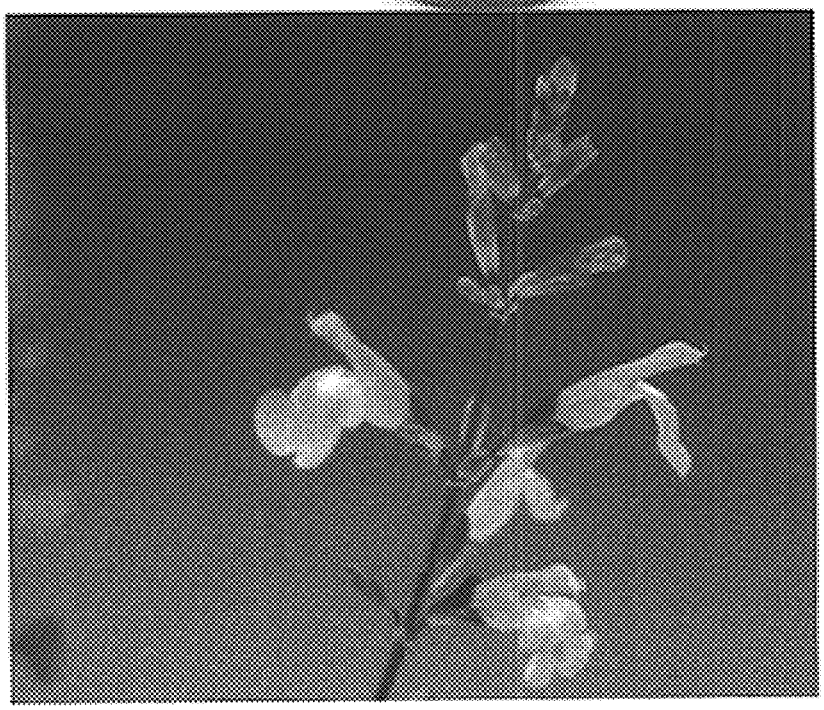

* * * * *